(12) United States Patent
Tominaga

(10) Patent No.: US 7,244,346 B2
(45) Date of Patent: Jul. 17, 2007

(54) CONCENTRATION MEASURING MECHANISM, EXPOSURE APPARATUS, AND DEVICE PRODUCTION METHOD

(75) Inventor: Yasuteru Tominaga, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 291 days.

(21) Appl. No.: 11/015,411

(22) Filed: Dec. 17, 2004

(65) Prior Publication Data

US 2005/0140943 A1 Jun. 30, 2005

(30) Foreign Application Priority Data

Dec. 26, 2003 (JP) .............................. 2003-434550

(51) Int. Cl.
*G01N 27/26* (2006.01)
*G01N 7/00* (2006.01)
*G03B 27/52* (2006.01)

(52) U.S. Cl. ........................ 204/424; 73/31.05; 355/30

(58) Field of Classification Search ................ 204/424; 355/30, 53; 73/23.34, 31.05; 422/83
See application file for complete search history.

(56) References Cited

U.S. PATENT DOCUMENTS 4,770,027 A * 9/1988 Ehara et al. ................ 73/23.34
5,872,721 A * 2/1999 Huston et al. ................ 702/24

FOREIGN PATENT DOCUMENTS

| JP | 11-087230 | 3/1999 |
| JP | 11-354409 | 12/1999 |
| JP | 2003-173964 | 6/2003 |

OTHER PUBLICATIONS

English Translation of JP 2003-173964 (dated Jun. 20, 2003).*
English Translation of JP 11-354409 (dated Dec. 24, 1999).*
English Translation of JP 11-087230 (dated Mar. 30, 1999).*

* cited by examiner

*Primary Examiner*—Alan Mathews

(57) ABSTRACT

In a concentration measuring mechanism, a first concentration meter that measures the concentration of a first gas inside an enclosed space is isolated by an isolator in an isolatable space isolated from the enclosed space in order to achieve high-precision measurement.

7 Claims, 11 Drawing Sheets

CONCENTRATION MEASURING MECHANISM, EXPOSURE APPARATUS, AND DEVICE PRODUCTION METHOD

BACKGROUND OF THE INVENTION

1. Field of the Invention

The present invention relates to an optical apparatus, such as an exposure apparatus, having a section that is purged by, for example, inactive gas in at least a part of an optical path leading through a reticle or the like from a light source to an object to be exposed, and also relates to a concentration measuring mechanism that measures the concentration of a certain gas contained in the inactive gas.

2. Description of the Related Art

Recently, integration density of semiconductor integrated circuits has increased, so that nano-order micromachining is required at present. For micromachining, exposure apparatuses are designed to have high cleanliness for stable exposure performance and are used in a clean environment such as a clean room, and the wavelength of light from a laser serving as an exposure light source is reduced. With the decrease in wavelength, however, exposure light causes impurities inside the exposure apparatus to photochemically react with oxygen ($O_2$), and a photoproduct produced by this photochemical reaction adheres to optical elements (e.g., lenses and mirrors). This fogs the lenses and mirrors, and reduces the illuminance.

In conventional exposure apparatuses using a KrF or ArF excimer laser as a light source, optical elements arranged on a laser optical path are housed in a space purged by inactive gas in order to prevent the illuminance from being reduced by the adhesion of the impurities to the lenses and mirrors, and to prevent a decrease in transmittance due to optical absorption by, for example, oxygen contained in the atmosphere in the optical path. Moreover, by monitoring the oxygen concentration of the interior, the degree of purging of the interior is detected, and it is determined whether exposure environment conditions are satisfied.

FIG. 8 is a schematic view of a part of an example of an exposure apparatus. A structure 101 serving as part of an optical system of the exposure apparatus has a lens unit 102 therein. Exposure light 106 is guided from a laser light source 105 to the outside of the structure 101 through sealing glass plates 103. Inactive gas is supplied into the structure 101 from one of pipes 107a and 107b, and is exhausted from the other pipe so that the interior of the structure 101 is constantly purged by clean inactive gas. A rotary member 108 has filters 109a and 109b for controlling the exposure light 106, and is driven by a motor 110. The motor 110 is fixed to the exposure apparatus by a motor holder 111. In this configuration, when the above-described photoproducts produced by photochemical reaction adhere to and fog the lens unit 102 and the light control filters 109a and 109b, the structure 101 is often opened to the atmosphere in order to replace the lens unit 102 and the light control filters 109a and 109b with new ones and to change the light control filters 109a and 109b to various types of filters for adjustment of the output of the exposure light. Therefore, the oxygen concentration inside the structure 101 frequently increases.

In the exposure apparatus, optical cleaning is performed to remove dirt from the optical elements. In optical cleaning, ozone is produced by injecting oxygen into the space occupied by the optical path, and the dirt is removed by the action of the ozone. After this maintenance operation, the oxygen concentration inside the structure 101 also increases.

Accordingly, an oximeter (oximeter) 112 shown in FIG. 8 or an oximeter 113 shown in FIG. 9 is provided to measure the oxygen concentration. By measuring the oxygen concentration inside the structure 101, it is determined whether the atmosphere inside the structure 101 is sufficiently replaced with inactive gas and does not have any influence on exposure performance. Exposure is started after the structure 101 is opened to the atmosphere based on this determination.

For example, Japanese Patent Laid-Open No. 11-087230 discloses an exposure apparatus in which stable exposure performance is maintained by monitoring the oxygen concentration with an oximeter provided inside the exposure apparatus.

Of the short-wavelength laser light used in the conventional exposure apparatuses, ArF laser light, which is absorbed by oxygen, provides a sufficient transmittance at an oxygen concentration of approximately 50 ppm to 100 ppm. For an oximeter that measures the oxygen concentration within the above range, the required measurement accuracy is approximately ±10 ppm to ±50 ppm. That is, in the conventional exposure apparatuses, since there is no need to measure a low oxygen concentration, the measurement is not taken into consideration. Therefore, even when the oximeter is exposed to the atmosphere containing a large amount of oxygen, since the measurement error of the oximeter is originally large, a phenomenon in which the measurement accuracy is decreased when the oximeter is exposed to the atmosphere containing oxygen having a concentration higher than the upper limit of the measurable concentration (hereinafter referred to as a high-concentration shock) does not substantially influence the measurement error. Therefore, it is unnecessary to consider the high-concentration shock.

However, the absorptance of oxygen for F2 laser light that is used in next-generation exposure apparatuses is more than or equal to 100 times the absorptance for ArF laser light. F2 laser light is absorbed not only by oxygen, but also by moisture. Therefore, in order to obtain an illuminance equivalent to that of ArF laser light, both the oxygen concentration and moisture concentration on the laser optical path in the exposure apparatus must be less than approximately 10 ppm, and must be managed and maintained at extremely low values. For that purpose, it is necessary to measure a low concentration with high precision (e.g., on the order of 0.1 ppm). However, as the performance of the concentration meter that can measure a low concentration increases, the concentration meter undergoes a greater high-concentration shock, and requires a long recovery time to be ready for precise measurement.

FIG. 7 is a graph that compares experimental values (broken line) obtained by measuring the oxygen concentration inside a chamber purged by inactive gas and calculated values (one-dot chain line) of the oxygen concentration inside the chamber. A chamber purged by inactive gas was opened for several minutes and was purged again, and the oxygen concentration of the atmosphere in the chamber was then measured. In a conventional method, the chamber was opened while an oximeter was left therein, and the measurement was taken after purging was started again. As shown in FIG. 7, when the exposure apparatus is opened for maintenance and filter replacement, the oximeter exposed to the atmosphere undergoes a high-concentration shock, and takes a long time to indicate precise measurement values. In some cases, the oximeter may break down.

For example, when it is assumed that exposure is started at a point A in FIG. 7, since the oximeter has not recovered yet from the high-concentration shock in the conventional measurement method, it shows a value higher than the actual concentration. Therefore, it is erroneously determined that the oxygen concentration has not been sufficiently reduced yet, and exposure cannot be started. Consequently, the downtime of the exposure apparatus is longer than necessary, and the exposure apparatus is stopped for a long period.

SUMMARY OF THE INVENTION

The present invention is directed to a concentration meter that can constantly measure the concentration of, for example, oxygen (or moisture, other substances) with high precision while being protected from a high-concentration shock.

In one aspect of the present invention, a concentration measuring mechanism operable to measure a concentration of a first gas in an enclosed space includes a first concentration meter that is configured to measure the concentration of the first gas inside the enclosed space; an isolatable space containing the first concentration meter; and an isolator having an isolation state in which the isolator isolates the first concentration meter in the isolatable space from the enclosed space and an open state in which the isolator allows communication between the enclosed space and the first concentration meter.

In one embodiment, the first concentration meter includes a first measuring section that reacts with the first gas.

In another embodiment, the first concentration meter includes a first measuring section containing a substance that reacts with the first gas.

In the open state, the isolator opens the first concentration meter to the enclosed space.

The isolator can open and isolate the isolatable space to and from the enclosed space.

In another embodiment, the concentration measuring mechanism further includes a gas supplier that supplies a second gas different from the first gas into the isolatable space.

In another embodiment, the concentration measuring mechanism further includes a substituting unit that substitutes a second gas, different from the first gas, in the isolatable space.

In another embodiment, a pressure in the isolatable space is higher than a pressure in the enclosed space when the isolator is in the isolation state in which the isolator isolates the first concentration meter in the isolatable space from the enclosed space.

In another embodiment, the concentration measuring mechanism further includes a second concentration meter that measures the concentration of the predetermined gas, wherein the first concentration meter is configured to measure the concentration within a first range and the second concentration meter is configured to measure the concentration within a second range different from the first range.

In another embodiment, a second upper limit of the second range is higher than a first upper limit of the first range.

In another embodiment, the second range does not overlap with the first range.

In another embodiment, a lower limit of the second range is higher than an upper limit of the first range.

In another embodiment, the concentration measuring mechanism further includes a second concentration meter that measures the concentration of the first gas, wherein the second concentration meter is provided inside the enclosed space and outside the isolatable space.

The first gas can be oxygen.

Further, the first gas can include moisture.

The isolator can include a valve provided between the enclosed space and the isolatable space.

A second aspect of the present invention provides an exposure apparatus that forms a pattern of a reticle onto an object. The apparatus includes a light source illuminating the reticle with light, and the above-described concentration measuring mechanism.

In one embodiment, the light source illuminates the reticle with light along an optical path and the enclosed space includes the optical path.

The exposure apparatus can include a movable optical element provided in the enclosed space.

A third aspect of the present invention provides a device production method including the steps of exposing an object with the above-described exposure apparatus; and developing the object exposed in the exposing step.

Further features and advantages of the present invention will become apparent from the following description of exemplary embodiments with reference to the attached drawings.

DESCRIPTION OF THE EMBODIMENTS

Embodiments of the present invention will be described below with reference to the attached drawings.

First Embodiment

Figure 1:
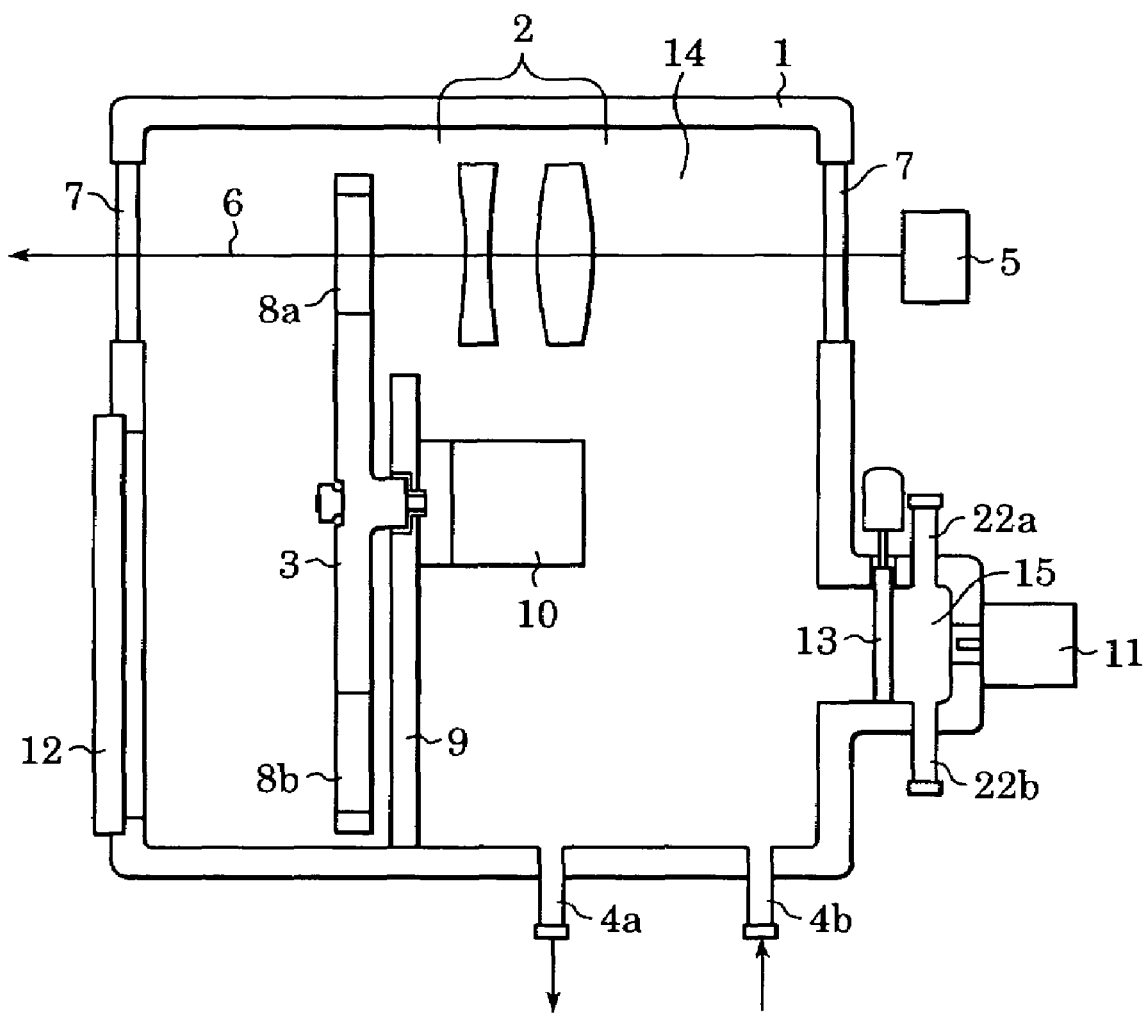
FIG. 1 is an explanatory view showing a first embodiment of the present invention in which an oximeter disposed inside an optical system is isolated in an isolation space when the interior of the optical system is opened to the atmosphere, and the isolation space is purged by inactive gas.

FIG. 1 shows a first embodiment of the present invention. In the first embodiment, an oximeter (first oximeter) is provided inside an optical system of an exposure apparatus whose interior is purged by inactive gas. When the interior of the optical system is opened to the atmosphere, the oximeter can be isolated from the interior of the optical system so as to be protected from the atmosphere.

A structure 1 serving as part of the optical system of the exposure apparatus has a lens unit 2 and a rotary member 3 therein. An interior 14 (enclosed space, inner space) of the structure 1 is purged by inactive gas that is exhausted and supplied through an inactive-gas exhaust pipe 4a and an inactive-gas supply pipe 4b. Exposure light 6 from a laser source 5 passes through sealing glass plates 7, the lens unit 2, and a first light control filter 8a mounted in the rotary member 3 to produce desired illumination light, and is guided out of the structure 1.

The rotary member 3 is driven by a motor 10 mounted on a motor holder 9, and switches between the first light control filter 8a and a second light control filter 8b, as necessary. A first oximeter 11 serves to measure the oxygen concentration inside 14 the structure 1 thus configured, and monitors the purging condition therein. When the lens unit 2 is replaced because it is fogged, and when the light control filters 8a and 8b are changed depending on the purpose of the usage, maintenance is performed while a maintenance door 12 is opened.

When the door 12 is opened for maintenance, the interior 14 of the structure 1 is exposed to the atmosphere, and the oxygen concentration inside the structure 1 increases to approximately 200,000 ppm (when it is assumed that the ratio of oxygen to the atmosphere is 20%). The first oximeter 11 used in the first embodiment is highly precise, and has a measurement range from 0.01 ppm to 1000 ppm. Therefore, if the first oximeter 11 is left in this state, it undergoes a high-concentration shock (the concentration measuring means or mechanism in the first embodiment is applied only when the concentration of gas to be measured is 1/100 or less or 1/1000 or less of the concentration the gas in the atmosphere). Accordingly, while the enclosed space 14 of the structure 1 is exposed to air, an isolation space (isolatable space) 15 is formed by using an air operation valve 13, and the first oximeter 11 (particularly, a measuring or sensing section of the meter, that is, a section that reacts with oxygen or a section containing a substance that reacts with oxygen) is placed inside the isolation space 15 so as to be isolated from the interior 14 exposed to air. When maintenance is finished, the door 12 is closed again, and purging by inactive gas is started, the air operation valve 13 is opened, and measurement of the oxygen concentration inside 14 the structure 1 is allowed to be started. The maintenance can be performed without exposing the first oximeter 11 to the atmosphere, and therefore, a high-concentration shock can be avoided. Since the air operation valve 13 can be arbitrarily opened and closed, it is opened after the concentration inside 14 the structure 1 reaches a predetermined value, and the measurement of concentration is then started. This makes the measurement more safe and precise. For example, the air operation valve 13 is not opened while the oxygen concentration inside 14 the structure 1 is more than or equal to 1000 ppm, which is the limit of the measurement value, immediately after purging is restarted, and is opened when the oxygen concentration reaches a predetermined concentration, for example, 500 ppm to 1000 ppm within the measurement range (measurable concentration range), and measurement is then started. This can reliably avoid a high-concentration shock.

The oxygen concentration inside 14 the structure 1 can also be measured with another oximeter (second oximeter not shown). The second oximeter is, of course, placed outside the above-described isolation space 15, and the measurement range thereof is set to be higher than 500 ppm to 1000 ppm. Also, the measurement range of the second oximeter can be higher than the upper limit of the measurement range of the first oximeter 11 disposed inside the isolation space, that is, the measurement range includes values ranging from the upper limit to the oxygen concentration of the atmosphere. However, it is satisfactory as long as the second oximeter has at least a part of the above range as the measurement range. Furthermore, the lower limit of the measurement range of the second oximeter can be higher than the upper limit of the measurement range of the first oximeter, and/or that the upper limit of the measurement range of the first oximeter be higher than the upper limit of the measurement range of the second oximeter, and/or that the measurement range of the first oximeter do not overlap with the measurement range of the second oximeter. The oximeter does not measure the concentrations in all the spaces in contact therewith, but measures the oxygen (gas) concentration in a space in contact with a specific portion of the oximeter. The specific portion is referred to as a measuring (sensing) section of the oximeter.

Since the oxygen concentration linearly changes in a high-concentration region and the change can be predicted easily, the valve may be automatically opened and the measurement of the oxygen concentration may be started, for example, when a predetermined time has passed since purging is started after the completion of maintenance (that is, after the purged space is exposed to the atmosphere).

An oximeter inactive-gas exhaust pipe 22a and an oximeter inactive-gas supply pipe 22b can be provided in the space 15 in which the first oximeter 11 is isolated by the air operation valve 13 (hereinafter referred to as an oximeter isolation space or an isolation space), as shown in FIG. 1. This allows the oximeter isolation space to be purged by inactive gas independently of the enclosed space 14 of the structure 1. Consequently, even when the structure 1 is opened to the atmosphere, inactive gas is constantly supplied to and exhausted from the oximeter isolation space 15. Therefore, the first oximeter 1 is more reliably protected. Gas supplied through the supply pipe 22b can be identical to inactive gas, nitrogen gas or helium gas, that is supplied into the enclosed space of the structure 1. Of course, a different kind of gas may be supplied. Alternatively, any gas that is different from gas whose concentration is measured by the first oximeter 11 (although the gas is oxygen in the embodiment, for example, moisture or carbon dioxide may be measured), that is, any gas whose concentration cannot be measured by the first oximeter 11 may be used.

When the pressure in the oximeter isolation space 15 is set higher than the internal pressure of the structure 1 by supplying inactive gas into the oximeter isolation space through the inactive-gas supply pipe 22b, even if the air operation valve 13 causes leakage while the structure 1 is exposed to atmosphere, the influence of the atmosphere can be reduced.

In the first embodiment, when the structure is exposed to the atmosphere, for example, for maintenance, the oximeter can be protected from high-concentration oxygen as in the atmosphere. Therefore, a high-concentration oxygen shock can be avoided, and the oxygen concentration can be precisely measured immediately after the completion of maintenance.

Figure 7:
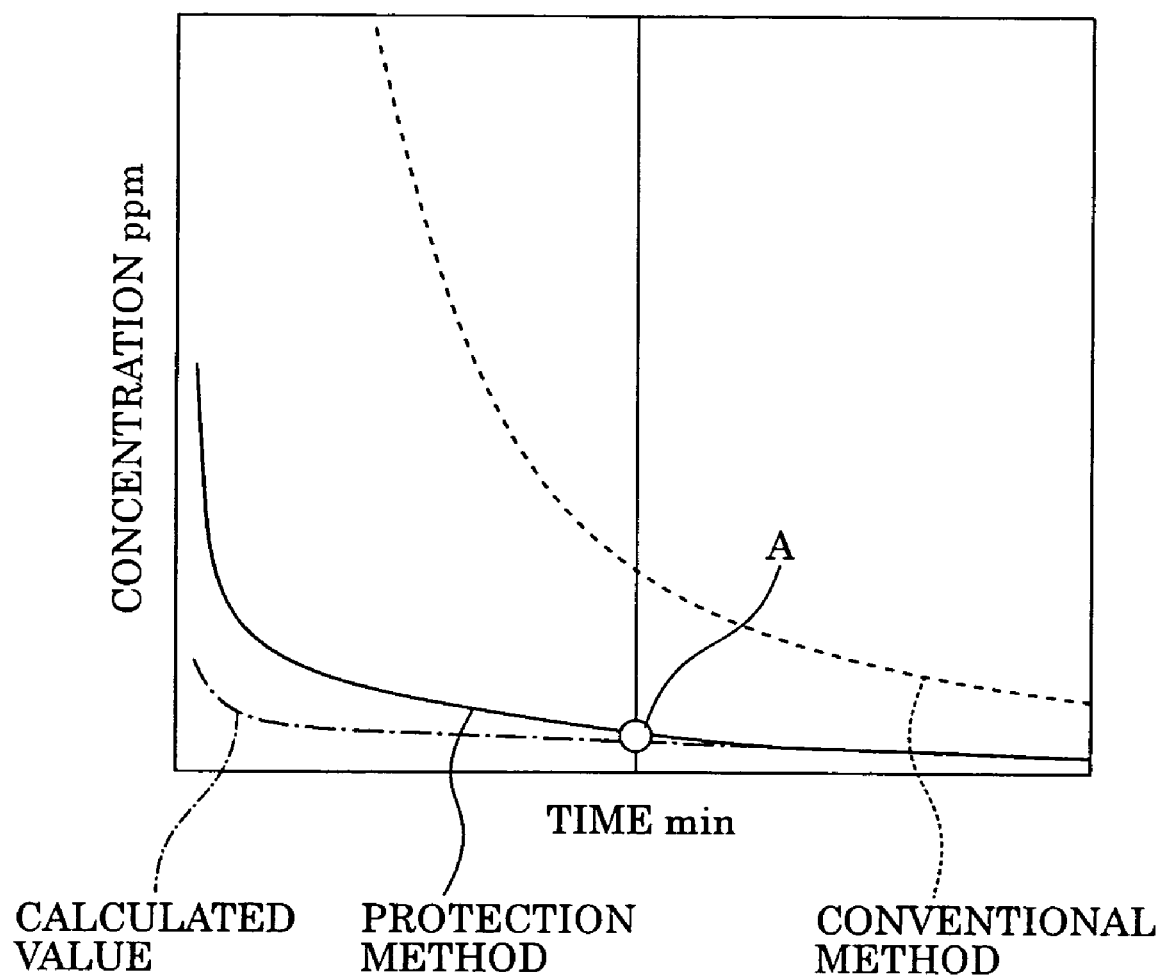
FIG. 7 is a graph that compares experimental values and calculated values of the oxygen concentration.
Figure 8:
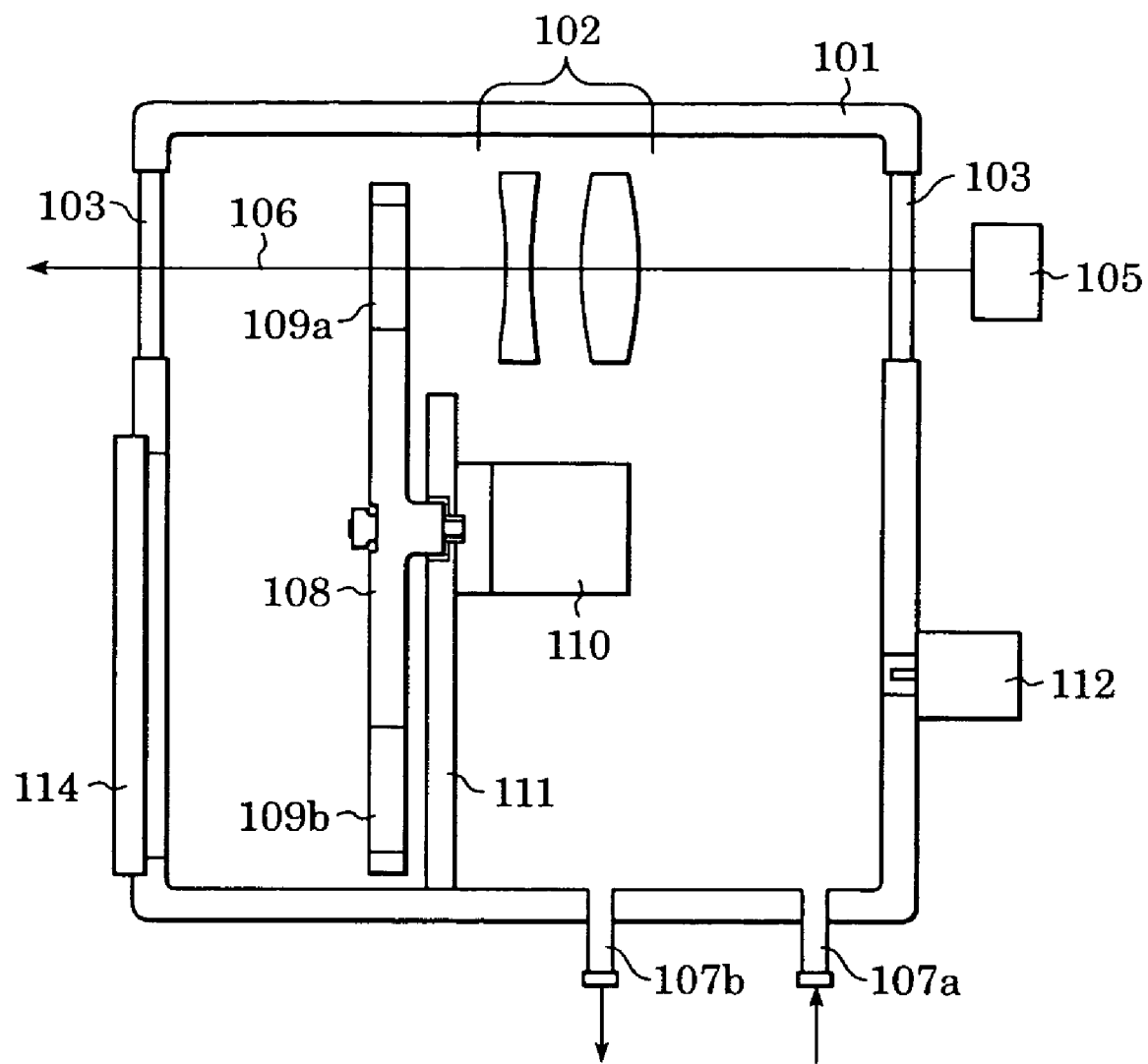
FIG. 8 is a schematic view showing a part of an example of a conventional exposure apparatus.
Figure 9:
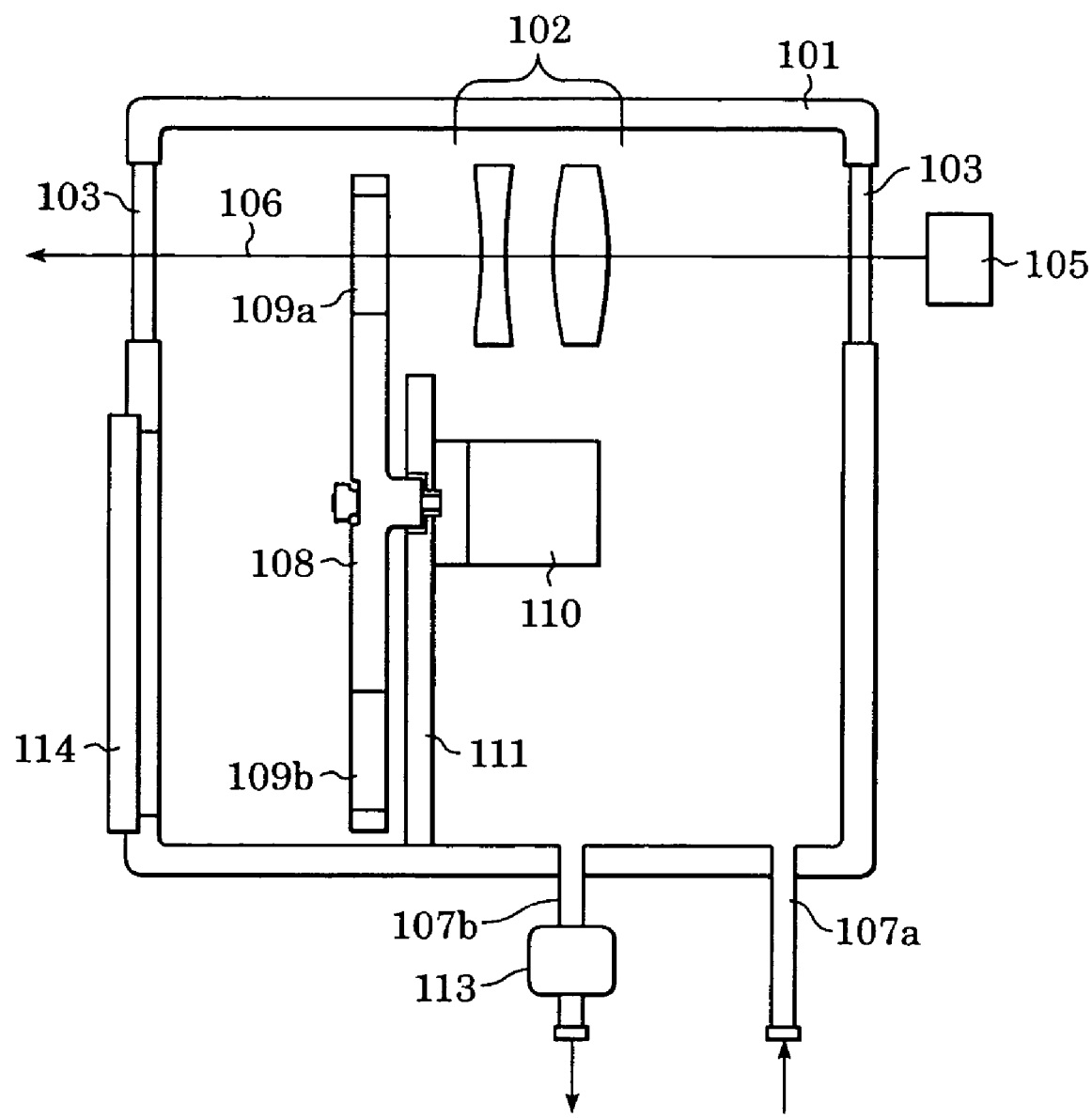
FIG. 9 is a schematic view showing a part of another example of a conventional exposure apparatus.

This advantage will be more specifically described with reference to FIG. 7. FIG. 7 is a graph that compares experimental values (broken line) obtained by measuring the oxygen concentration inside a chamber purged by inactive gas, calculated values (one-dot chain line) of the oxygen concentration inside the chamber, and the oxygen concentration (solid line) obtained in a protection method (the method of the first embodiment). A chamber purged by inactive gas was opened for several minutes and was then purged again, and the oxygen concentration in the atmosphere inside the chamber was measured. In the conventional method, the chamber was opened and purged again while the oximeter was left therein. As shown in FIG. 7, the oximeter is protected from a high-concentration shock in the protection method (solid line) of the first embodiment, and can constantly measure the concentration with high precision. That is, in the protection method (solid line), while the chamber was opened, the oximeter was protected by being isolated in a space (isolation space) different from the enclosed space, and the isolation space surrounding the oximeter was filled with inactive gas supplied from a supply pipe different from the supply pipe through which inactive gas is supplied into the enclosed space (the isolation space was purged, that is, the oxygen concentration inside the isolation space was reduced or maintained within the measurable concentration range of the oximeter). After purging of the enclosed space was restarted, the measurement was taken. While the experimental values in the conventional method are widely different from the theoretical values, the measured values in the protection method substantially coincide with the calculated values. The measured values do not completely coincide because a calculation expression for finding the theoretical values is established without consideration of, for example, the amount of outgas from the chamber. From the above, it is evident that the measured values become seriously wrong even when the oximeter is influenced by the atmosphere for only several minutes.

Second Embodiment

Figure 2:
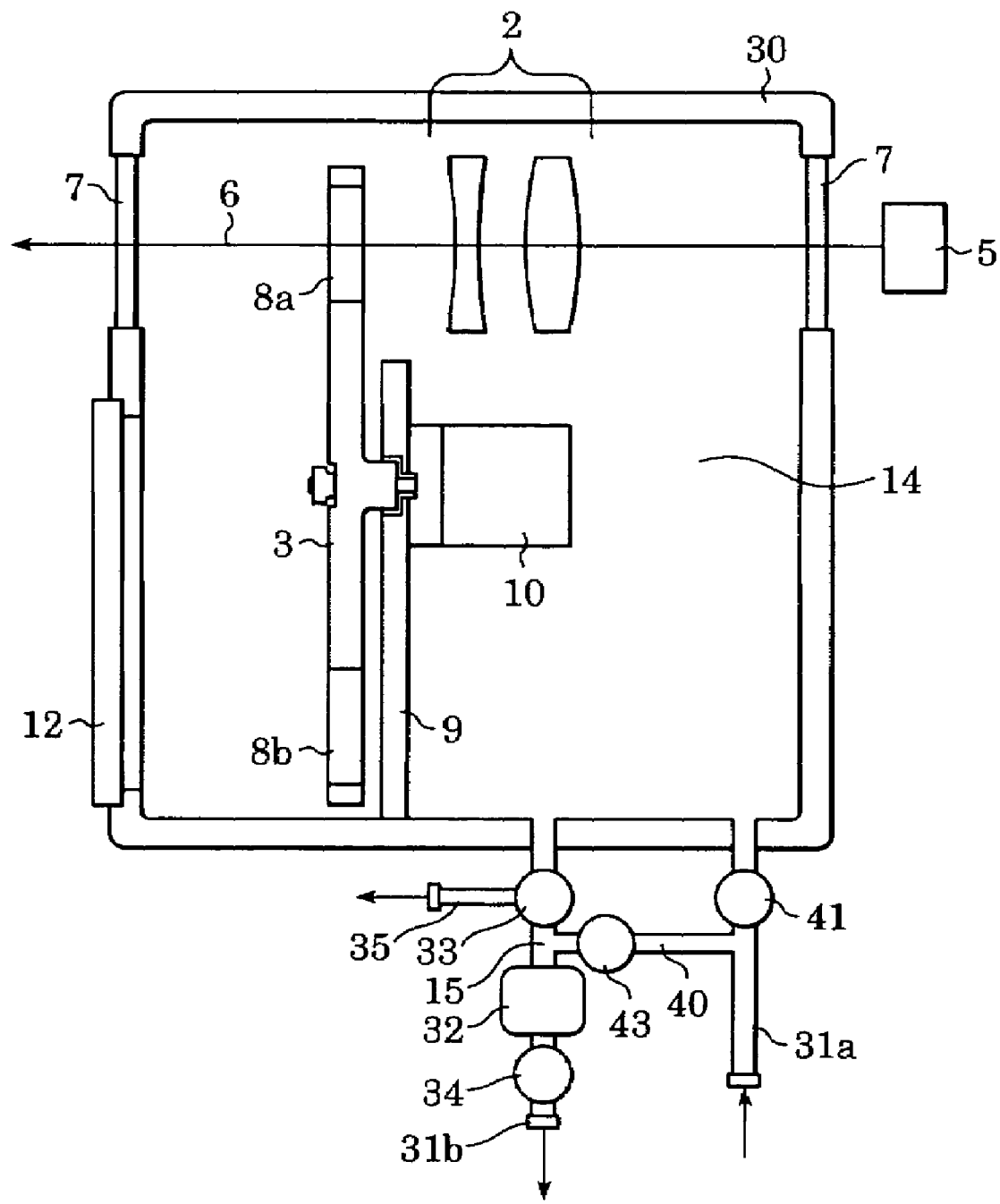
FIG. 2 is an explanatory view showing a second embodiment of the present invention in which an oximeter for measuring the oxygen concentration of an inactive gas space is purged by inactive gas when the space is opened to the atmosphere.

FIG. 2 shows a second embodiment of the present invention. When the interior of the optical system is opened to the atmosphere, the oximeter is isolated from the interior so as to be protected from the atmosphere. In a manner similar to that in the first embodiment, the interior 14 of a structure 30 serving as part of an optical system of an exposure apparatus is purged by inactive gas that is supplied and exhausted through an inactive-gas supply pipe 31a and an inactive-gas exhaust pipe 31b. An oximeter 32 measures the oxygen concentration of gas exhausted through the inactive-gas exhaust pipe 31b. Sealing valves 33 and 34 are provided on both intake and exhaust sides of the oximeter 32. When the interior 14 of the structure 30 is opened to the atmosphere, the valves 33 and 34 are closed to form an isolation space (isolatable space) 15 in which the oximeter 32 is protected. Moreover, when purging of the structure 30 by inactive gas is restarted, the oximeter 32 can be protected by performing exhausting through an exhaust pipe 35 provided at the valve 33 until the inner oxygen concentration is reduced to a predetermined concentration that does not cause a high-concentration shock. As described in the first embodiment, since the change in concentration in a high-concentration region can be easily predicted, the valves may be automatically switched and the measurement of the oxygen concentration may be started when a predetermined time has passed from the start of purging.

As shown in FIG. 2, a connecting pipe 40 is provided between the pipes 31a and 31b through which inactive gas is supplied into and exhausted from the structure 30. When inactive gas is not supplied to the structure 30, the valves 41 and 33 are closed and a valve 43 mounted at the connecting pipe 40 is opened. Accordingly, the isolatable space surrounding the oximeter 32 can be isolated from the interior of the structure, and the oxygen concentration in the isolatable space surrounding the oximeter 32 can be reduced by supplying the inactive gas to the isolatable space. The oximeter can be protected from the atmosphere.

Figure 3:
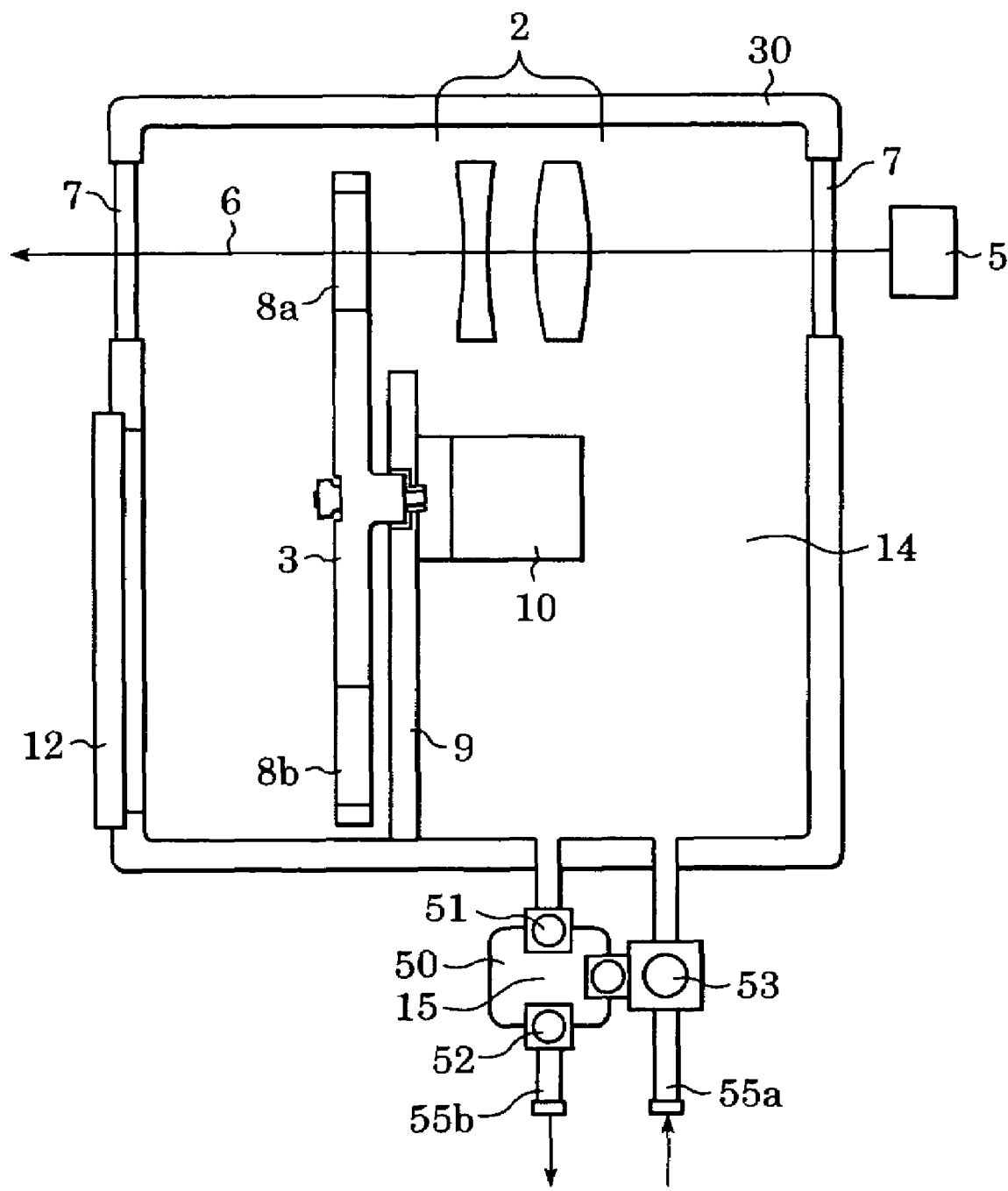
FIG. 3 is an explanatory view showing a modification of the second embodiment in which the structure in the second embodiment is applied to an oximeter.

FIG. 3 shows a modification of the second embodiment. In this modification, the function in the second embodiment is applied to an oximeter.

An oximeter 50 includes valves 51, 52, and 53 having a channel-switching function and a block function. The valves 51 and 52 connect an enclosed space 15 inside a structure 30, the oximeter 50, and a gas exhaust pipe 55b, and the valve 53 connects the enclosed space 15 in the structure 30 and a gas supply pipe 55a. The oxygen concentration of gas inside 14 the structure 30 is measured with the valves 51 and 52 open. When the structure 30 is opened to the atmosphere, the valves 51, 52 and 53 are closed to isolate the oximeter 50 from the interior (to isolate the isolatable space surrounding the oximeter from the interior opened to the atmosphere), or the valve 51 is closed and the valves 52 and 53 are opened to isolate the oximeter 50 from the interior (to isolate the isolatable space surrounding the oximeter from the interior opened to the atmosphere) and supply inactive gas to the isolatable space surrounding the oximeter. This prevents a measuring section inside the oximeter 50 from being exposed to the atmosphere. When purging of the interior 14 of the structure 30 by inactive gas is restarted and the oxygen concentration is measured, exhausting may be performed through an exhaust valve (not shown) provided at the valve 51, and measurement may be started after the oxygen concentration reaches a predetermined concentration.

Since the oximeter has the protecting function in this modification, a high-concentration shock can be prevented and high-precision measurement can be taken without providing any special sealing mechanism for the object to be measured.

According to the second embodiment, the oximeter can also be protected from the atmosphere, in a manner similar to that in the first embodiment. When the structure is opened to the atmosphere, for example, for maintenance, since the oximeter can be protected from a high-concentration oxygen in the atmosphere, a high-concentration oxygen shock can be avoided.

Third Embodiment

Figure 4:
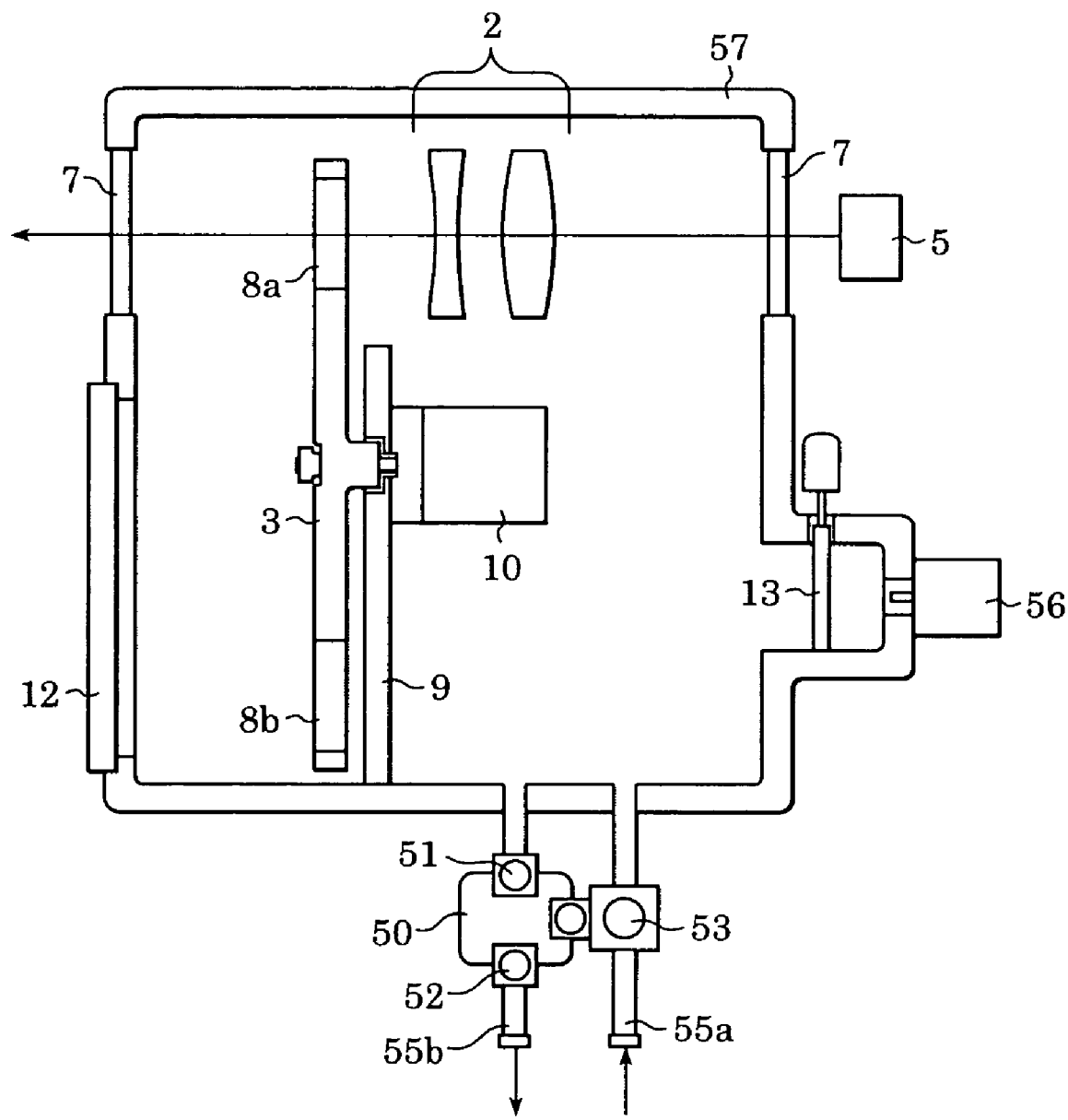
FIG. 4 is an explanatory view showing a third embodiment of the present invention in which the structures in the first and second embodiments are applied to oximeters.

FIG. 4 shows a third embodiment of the present invention to which the first and second embodiments are both applied.

For example, when a door 12 is opened in order to exchange a lens unit 2 or a light adjustment filter 8a or 8b, an air operation valve 13 is closed, thereby a rough-measurement oximeter 56 is isolated from the interior (disposed in the isolatable space isolated from the interior). Simultaneously, a valve 51 provided at an oximeter 50 is closed to isolate the oximeter 50 from the interior (to isolate the oximeter 50 in the isolatable space isolated from the interior) so as to prevent the oximeter 50 from being exposed to the atmosphere (high-concentration oxygen). In addition, a channel of inactive gas is switched by a valve 53 to supply the inactive gas to the oximeter 50 (and the isolatable space surrounding the interior), so that the oxygen concentration in the isolatable space surrounding the oximeter 50 is further reduced.

When the door 12 is closed at the completion of maintenance, the valve 53 is switched, and inactive gas is also supplied into a structure 57. Then, the air operation valve 13 is opened, and the concentration inside the structure 57 is measured with the rough-measurement oximeter 56. When the measured concentration comes in the measurement range, supply of inactive gas by the valve 53 is stopped, the valve 51 is opened, and precise measurement with the oximeter 50 is started.

Although the concentration change inside a purged chamber is easily predicted in a high-concentration region, the prediction becomes more difficult as the concentration decreases. For this reason, for example, when a precise oximeter is used which is suited for use in the concentration of 100 ppm or less, rough measurement is taken with an oximeter having a high-concentration measurement range, and it is determined whether the range does not give a high-concentration shock to the precise oximeter. This makes it possible to more reliably avoid a high-concentration shock. Accordingly, this problem can be completely overcome by adopting the third embodiment.

According to the third embodiment, it is possible to reliably avoid the concentration that gives a high-concentration shock and to completely prevent the high-concentration shock. Therefore, precise measurement of the concentration can be taken immediately after the completion of maintenance during which the structure must be opened to the atmosphere.

Fourth Embodiment

Figure 5:
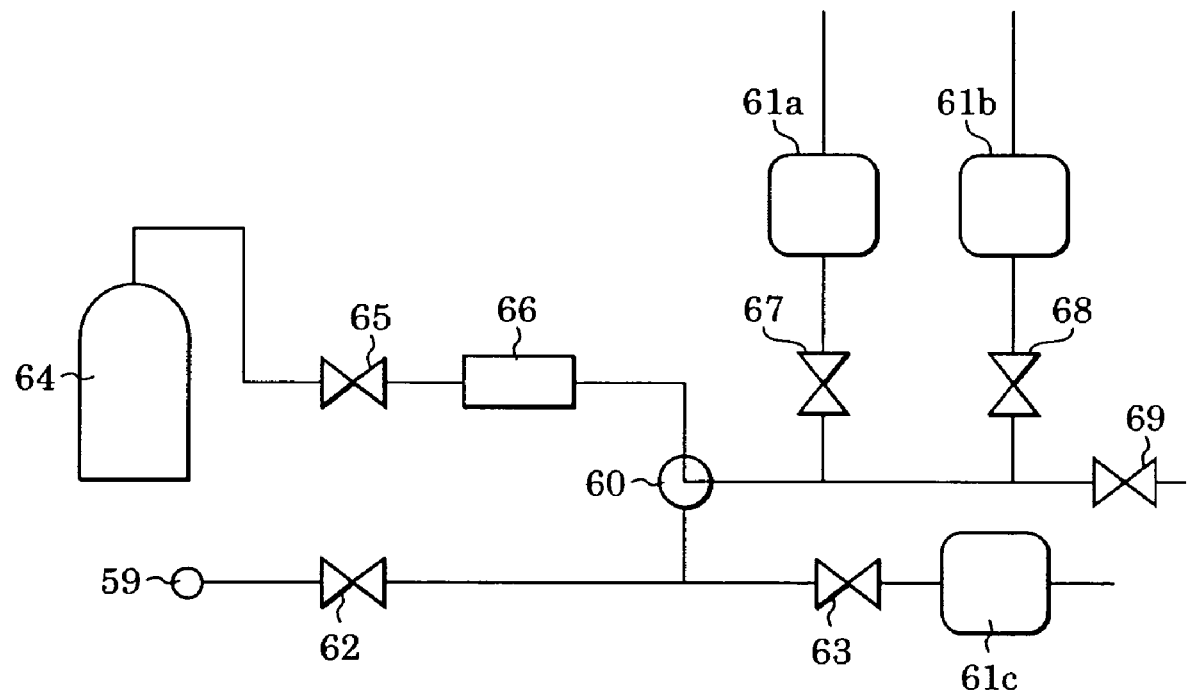
FIG. 5 is a piping diagram of a concentration measuring mechanism according to a fourth embodiment of the present invention.

FIG. 5 is a piping diagram of a concentration measuring mechanism of the present invention.

An object to be measured is mounted at a mounting port 59. Measuring gas flows through a three-way valve 60, and the flow rate of the gas is optimized by flow-rate adjustment valves 67 and 68. The measuring gas is guided to a (precise) oximeter 61a and a moisture concentration meter 61b, and surplus measuring gas (gas including a gas to be measured, for example, oxygen) is exhausted through a valve 69. While only the oximeter and the moisture concentration meter are described herein, other concentration meters for desired gasses to be measured may be connected in parallel.

While the measurement object is exposed to the atmosphere (high-concentration oxygen), valves 62 and 63 may be closed so as not to have an influence (damage that can cause measurement errors) on the oximeter 61a and the moisture concentration meter 61b. Thus, the oximeter 61a and the moisture concentration meter 61b can be isolated from the interior (the isolatable space surrounding the oximeter 61a and the moisture concentration meter 61b can be isolated from the interior) by closing the valves 62 and 63. Therefore, the oximeter 61a and the moisture concentration meter 61b are prevented from being exposed to the atmosphere (high-concentration oxygen, high-concentration moisture, etc.) Immediately after purging of the measurement object is restarted after the exposure, or when it is predicted that the oxygen concentration of the measuring gas is high, the concentration may be monitored by a rough-measurement oximeter 61c, and gas to be measured may be exhausted by opening the valve 63 until the concentration reaches a predetermined value. The gas is supplied from an inactive-gas supplier 64, is adjusted by a valve 65 and a pressure controller 66, and is supplied to the oximeter 61a and the moisture concentration meter 61b by switching the three-way valve 60. In this configuration, the concentration meters are not exposed to the atmosphere, and constantly hold the oxygen concentration and the moisture concentration in a low state.

According to the fourth embodiment, the concentration meters can constantly take high-precise measurement.

Fifth Embodiment

Figure 6:
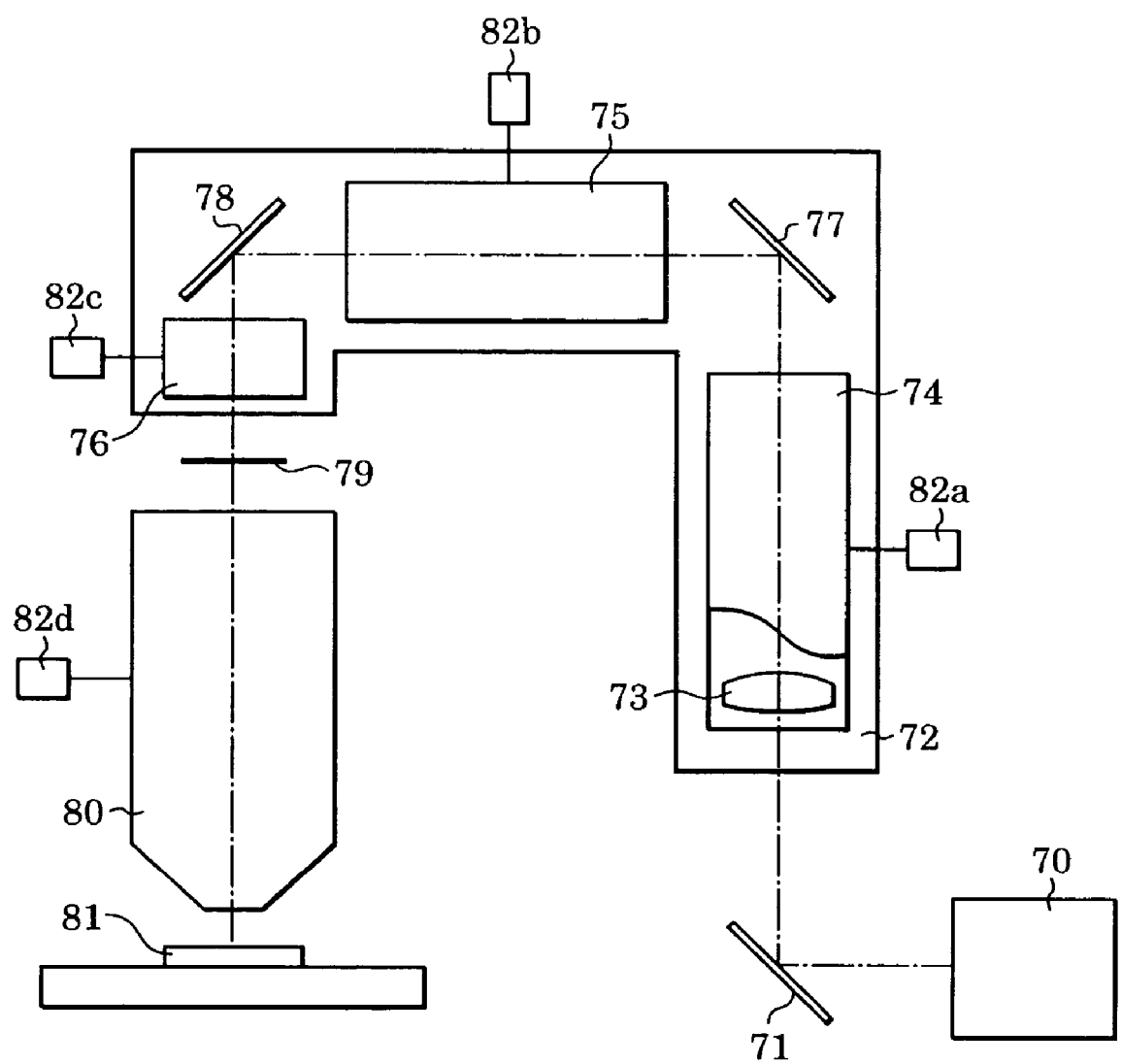
FIG. 6 is an explanatory view of an exposure apparatus according to a fifth embodiment of the present invention.

FIG. 6 is a schematic view of an optical system of an exposure apparatus according to a fifth embodiment of the present invention. Exposure light emitted from a laser source 70 is caused by a mirror 71 to enter an illumination unit 72. Illumination barrels 74, 75, and 76 including, for example, a lens 73 are arranged inside the illumination unit 72. The exposure light is guided to a reticle 79 by barrels 74, 75, and 76 and by mirrors 77 and 78. Subsequently, a pattern of the reticle 79 is formed on a wafer surface 81 by a projection unit 80.

In the fifth embodiment, oximeters 82a, 82b, 82c, and 82d equivalent to the meters in the above-described first to fourth embodiments are mounted, respectively, at the illumination barrels 74, 75, and 75 and the projection unit 80. Therefore, the concentration of the atmosphere inside the exposure apparatus can be measured precisely.

In a case in which the oximeters are provided in the respective units, as shown in FIG. 6, for example, when the illumination barrel 74 is opened for maintenance, only the oximeter 82a is protected. Gas exhausted after other units are purged is used as purging gas to be supplied to the oximeter 82a for protection. This can save inactive gas used for purging.

According to the fifth embodiment, the oxygen concentration of the exposure atmosphere can be precisely measured by applying the meters of the first to fourth embodiments to the optical system shown in FIG. 6. This enhances the availability of the exposure apparatus.

Sixth Embodiment

A device production method using the above-described exposure apparatus will be described as a sixth embodiment with reference to FIGS. 10 and 11.

Figure 10:
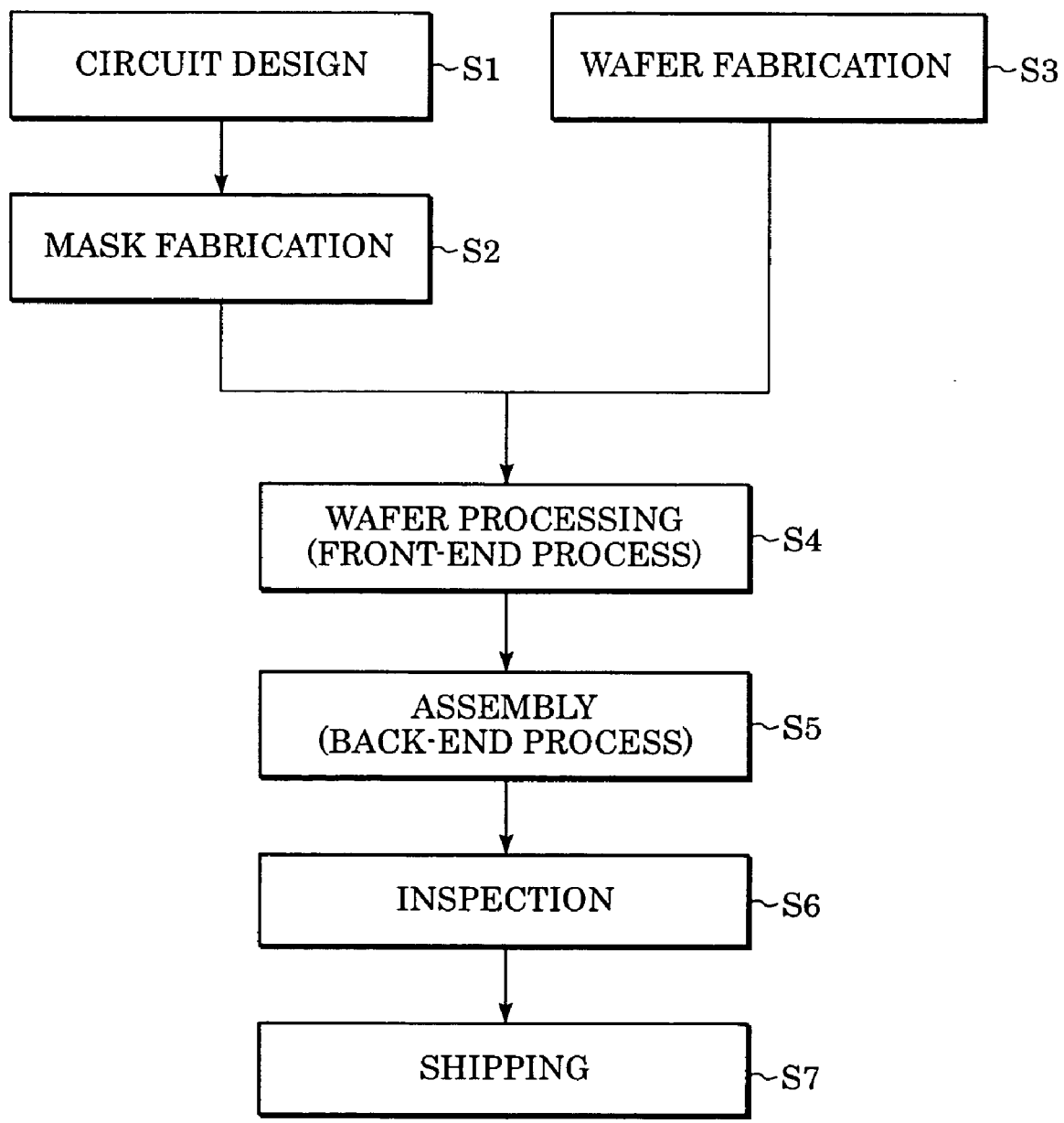
FIG. 10 is a flowchart showing a device production method according to a sixth embodiment of the present invention.

FIG. 10 is a flowchart showing the production of devices (for example, semiconductor chips such as ICs, LSIs, LCDs, and CCDs). In the sixth embodiment, production of semiconductor chips will be described as an example. In Step S1 (circuit design), a circuit of semiconductor chips is designed. In Step S2 (mask fabrication), a mask is fabricated in the designed circuit pattern. In Step S3 (wafer fabrication), a wafer is formed of a material such as silicon. In Step S4 (wafer process), called a front-end process, actual circuits are formed on the wafer by lithography with the mask and the wafer. In subsequent Step S5 (assembly), called a back-end process, semiconductor chips are formed from the wafer obtained in Step S4. This process includes, for example, an assembly process (dicing and bonding) and a packaging process (chip sealing). In Step S6 (inspection), the semiconductor chips obtained in Step S5 are tested for, for example, operation and durability. The semiconductor chips are thus completed through the above processes, and are then shipped (Step S7).

Figure 11:
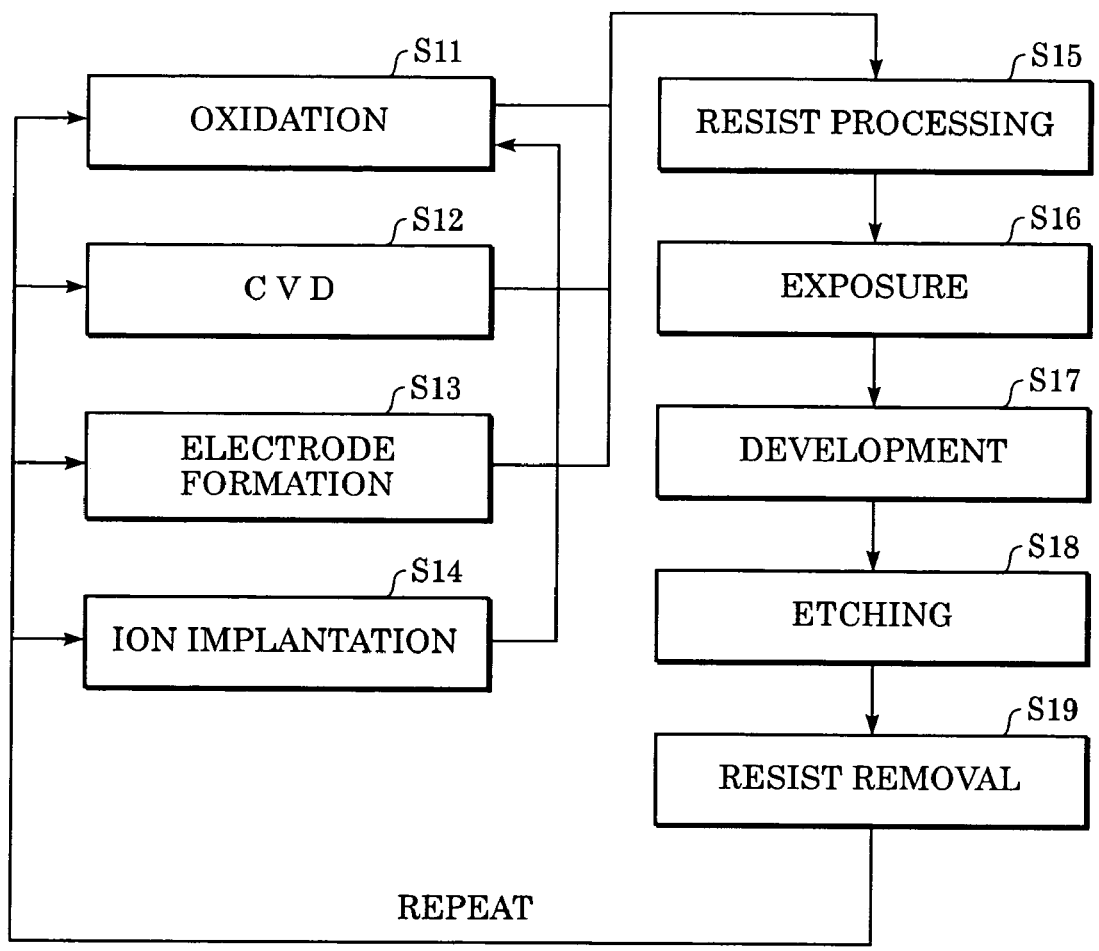
FIG. 11 is a detailed flowchart showing a wafer process in Step 4 shown in FIG. 10.

FIG. 11 is a detailed flowchart of the wafer process in Step S4 shown in FIG. 10. In Step S11 (oxidation), the surface of the wafer is oxidized. In Step S12 (CVD), an insulating film is formed on the surface of the wafer. In Step S13 (electrode formation), electrodes are formed. In Step S14 (ion implantation), ions are implanted in the wafer. In Step S15 (resist processing), a photosensitive agent is applied to the wafer. In Step S16 (exposure), the circuit pattern of the mask is projected onto the wafer by the exposure apparatus. In Step S17 (development), the exposed wafer is developed. In Step S18 (etching), parts other than the developed resist image are etched away. In Step S19 (resist removal), the resist, which has become unnecessary due to etching being completed, is removed. By repeating these steps, a multi-layer circuit pattern is formed on the wafer. The device production method of the sixth embodiment can produce devices of higher quality than in the conventional methods. In this way, the present invention covers the device production method using the exposure apparatus, and devices as products.

As described above, in the above embodiments of the present invention, a high-precision concentration meter, such as an oximeter, used in the exposure apparatus can be protected from the atmosphere when an object to be measured is opened to the atmosphere, for example, for maintenance, a high-concentration shock can be avoided, and high-precision measurement can be restarted immediately.

In particular, in an exposure apparatus using a short-wavelength laser light, such as F2 laser light, which is absorbed by oxygen and moisture, the concentration of a small amount of oxygen can be precisely measured immediately after maintenance. Therefore, it is possible to save a wasteful waiting time taken until the concentration meter recovers.

By these effects, it is possible to reduce the initial startup time of the exposure apparatus and the startup time after maintenance. Therefore, according to the present invention, it is possible to enhance the availability and reliability of the exposure apparatus.

When the enclosed space is opened to the atmosphere, inactive gas is supplied into the above-described isolation space (isolatable space) in order to protect the meter. Therefore, it is possible to prevent the oxygen and moisture concentrations inside the isolation space from being increased by leakage and outgas from the isolation structure, and to reliably avoid a high-concentration shock. Even if leakage occurs because of insufficient sealing after isolation in the above configuration, the atmosphere that enters the meter can be reduced. The meter can be more safely protected by using the isolation mechanism for isolating the meter (particularly, a section that senses oxygen) in the isolation space isolated from high-concentration oxygen or oxygen of a concentration higher than the upper limit of the measurable range, in combination with the gas substituting mechanism defined by, for example, the oximeter inactive-gas exhaust pipe 22a and the oximeter inactive-gas supply pipe 22b described above.

Since the concentration inside the enclosed space can be roughly measured, it is possible to determine whether the concentration adversely affects the precise concentration meter before measurement is taken with the precise concentration meter. Therefore, it is possible to safely measure the oxygen concentration with the precise concentration meter that is seriously influenced by a high-concentration shock.

Since the concentration meter itself has the protection mechanism, a special structure does not need to be provided for the object to be measured. For this reason, precise measurement can be taken regardless of the structure of the object.

When the exposure apparatus is exposed to the atmosphere, for example, for maintenance, the concentration of a small amount of oxygen can be precisely measured immediately after maintenance. Therefore, it is possible to save a wasteful waiting time taken until the oximeter recovers from a high-concentration shock, and to enhance the reliability and availability of the exposure apparatus.

The above-described embodiments may be combined in any manner as long as there is no contradiction. Furthermore, the lens and the mirror in the embodiments may be referred to a refracting optical system and a reflecting optical system, or may be both referred to simply as "optical elements".

When the concentration measuring mechanism and the exposure apparatus are configured as in the above embodiments, it is possible to quickly measure the concentration at the initial startup of an apparatus to be measured and at the startup after maintenance.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2003-434550 filed Dec. 26, 2003, which is hereby incorporated by reference herein.

What is claimed is:

1. A concentration measuring mechanism operable to measure a concentration of a first gas in an enclosed space, comprising:
   a first concentration meter configured to measure the concentration of the first gas inside the enclosed space;
   an isolatable space containing the first concentration meter;
   an isolator having an isolation state in which the isolator isolates the first concentration meter in the isotatable space from the enclosed space and an open state in which the isolator allows communication between the enclosed space and the first concentration meter; and
   a gas supplier communicating with the isolatable space and operable to supply a second gas different from the first gas into the isolatable space.

2. A concentration measuring mechanism operable to measure a concentration of a first gas in an enclosed space, comprising:
   a first concentration meter configured to measure the concentration of the first gas inside the enclosed space;
   an isolatable space containing the first concentration meter;
   an isolator having an isolation state in which the isolator isolates the first concentration meter in the isolatable space from the enclosed space and an open state in which the isolator allows communication between the enclosed space and the first concentration meter;
   a substituting unit operable to substitute a second gas, different from the first gas, in the isolatable space.

3. A concentration measuring mechanism operable to measure a concentration of a first gas in an enclosed space, comprising:
   a first concentration meter configured to measure the concentration of the first gas inside the enclosed space;
   an isolatable space containing the first concentration meter; and an isolator having an isolation state in which the isolator isolates the first concentration meter in the isolatable space from the enclosed space and an open state in which the isolator allows communication between the enclosed space and the first concentration meter, wherein a pressure in the isolatable space is higher than a pressure in the enclosed space responsive to the isolator being in the isolation state in which the isolator isolates the first concentration meter in the isolatable space from the enclosed space.

4. A concentration measuring mechanism operable to measure a concentration of a first gas in an enclosed space, comprising:

a first concentration meter configured to measure the concentration of the first gas inside the enclosed space;

an isolatable space containing the first concentration meter;

an isolator having an isolation state in which the isolator isolates the first concentration meter in the isolatable space from the enclosed space and an open state in which the isolator allows communication between the enclosed space and the first concentration meter; and a second concentration meter configured to measure the concentration of the first gas, wherein the first concentration meter is configured to measure the concentration within a first range and the second concentration meter is configured to measure the concentration within a second range different from the first range.

5. The concentration measuring mechanism according to claim 4, wherein a second upper limit of the second range is higher than a first upper limit of the first range.

6. The concentration measuring mechanism according to claim 4, wherein the second range does not overlap with the first range.

7. The concentration measuring mechanism according to claim 4, wherein a lower limit of the second range is higher than an upper limit of the first range.

* * * * *